United States Patent [19]

Lustgarten

[11] 4,295,941
[45] Oct. 20, 1981

[54] METHOD OF MANUFACTURING A METAL CERAMIC DENTAL RESTORATION

[75] Inventor: Stewart J. Lustgarten, Holliston, Mass.

[73] Assignee: Healthco Inc., Boston, Mass.

[21] Appl. No.: 101,203

[22] Filed: Dec. 7, 1979

[51] Int. Cl.$^3$ .............................................. A61C 5/08
[52] U.S. Cl. .............................. 204/35 R; 204/37 R; 204/38 S; 204/38 C; 433/207; 433/222
[58] Field of Search ................ 204/35 R, 38 S, 38 C, 204/37 R; 427/330, 2, 376.4; 433/207, 208, 206, 222, 200

[56] References Cited

U.S. PATENT DOCUMENTS

| | | | |
|---|---|---|---|
| 3,585,064 | 6/1971 | Prosen | 427/374.2 |
| 3,934,348 | 1/1976 | Janjic | 433/222 |
| 4,125,442 | 11/1978 | Rogers | 204/38 C |

*Primary Examiner*—Delbert E. Gantz
*Assistant Examiner*—William Leader

[57] ABSTRACT

The method of the present invention involves fabricating a cast metal framework from a non-precious metal alloy containing nickel, electroplating a thin film of gold over a predetermined surface area of the framework, distributing finely divided gold particles of varying size about the electroplated surface and firing successive layers of porcelain over the predetermined surface area.

5 Claims, No Drawings

METHOD OF MANUFACTURING A METAL CERAMIC DENTAL RESTORATION

This invention relates to a method for forming a porcelain to metal restoration in the manufacture of dental prostheses.

Dental restorations such as crowns and bridges are conventionally fabricated using a cast metal framework with a porcelain ceramic veneer. The metal framework provides the restoration with the necessary strength required to withstand the forces and stresses experienced in the mouth when biting food. The porcelain veneer simulates the natural tooth enamel. Porcelain as used in dentistry, is composed of natural feldspar, quartz and kaolin with small additions of other materials such as coloring agents. The porcelain material is conventionally applied to the metal understructure in successive layers. After the application of each layer, the structure is fired in a radiant furnace generally in a vacuum at elevated temperatures. The composition of the metal framework must be workable, have a relatively high tensile strength and be resistant to oral fluids. Noble metals particularly gold satisfies the requirements for the metal understructure and provides, in addition, a yellow reflective surface which is aesthetically desirable.

Due, however, to the recent explosive increase in the price of gold and other noble metals the use of non-precious metal compositions have been suggested. The use of non-precious metals as an alternative to noble metals for fixed prosthodontic devices is not new. In fact, there has been substantial research conducted on this subject in the areas of fabrication, marginal fit, aesthetics and adherence. It has been established that conventional non-precious metal compositions are not compatible with porcelain resulting in interfacial stresses which apparently develop from differences in the coefficients of thermal contraction of the porcelain and metal after fusion at elevated temperatures. This readily leads to porcelain fracture and separation from the metal framework. Non-precious metals also lack the yellow gold background provided by gold which cannot be satisfactorily simulated by adding coloring agents to the metal composition.

Accordingly, it is the principal object of the present invention to provide a method for forming a porcelain to metal restoration using a cast non-precious metal framework.

It is a further object of the present invention to provide a method for forming a porcelain to metal restoration using a cast non-precious metal framework which provides a reflective yellow gold background.

It is an even further object of the present invention to provide a method for forming a porcelain to non-precious metal restoration in which the adherence between the non-precious metal structure and the porcelain veneer is enhanced through the use of retention particles distributed intermediate the porcelain and nickel structures.

The method of the present invention comprises; forming a metal casting from a non-precious metal composition containing at least four percent nickel; electroplating a thin film deposit of gold over said casting of from about 0.04 to 1 mil in thickness, applying a coating of finely divided particles of gold of varying size over said electroplated gold deposit and firing successive layers of porcelain over the layer of gold particles at an elevated temperature.

In accordance with the present invention any non-precious metal composition may be employed to form the metal understructure of the restoration such as for example, a crown, bridge or denture. A particularly suitable understructure is of the following composition by weight: 20–25% Cr, 1.7% Be, about 70–75% Ni with trace elements of Fe, Si, C and B. The understructure may be formed following any conventional procedure such as casting.

The amount of nickel present in the metal understructure should represent at least four percent of the total composition by weight although a minumum of 20% is preferred. A minimum presence of nickel is essential to satisfactorily establish a bond between the understructure and a thin film deposit of electroplated gold. Any conventional electroplating procedure may be used to form the electroplated gold deposit. The gold deposit should form a coating of from 0.04 to 1 mil in thickness. The preferred electroplating procedure involves brush electroplating using commercially available equipment such as is commercially sold through Parkell, Inc. The electroplating operation may be performed with any conventional gold containing electrolyte although a boric acid electrolyte containing a gold alloy including platinum and palladium in a sodium and potassium salt solution is preferred. The gold is deposited as a thin film layer of from about 0.04 to 1 mil to provide a continuous uniform matrix which adheres to the non-precious metal surface. The adhesion is believed to be promoted by the nickel constituent in the conventional non-precious metal composition.

The electroplated gold surface is thereafter substantially covered with finely divided particles of gold. The finely divided particles may be in the form of flakes or other particulate forms in a varying size range distribution of preferably between 1 to about 20 microns in size. The gold particles may be alloyed with other noble metals such as silver and may include minor amounts of boron, aluminum, magnesium, copper and silica. It is preferred that the particles be suspended in a carrier which will volatilize during the firing of the porcelain leaving a widely dispersed distribution of gold restoration. Alternatively, the particles may be scattered over the electroplated surface to form a nonuniform discontinuous layer. The firing of porcelain generally falls in a range between 1600° F. to 1900° F. In this range the finely divided gold particles will form beads which provides a retentive surface structure for the porcelain. The gold particles in turn are strongly cemented to the underlying gold electroplated deposit. Any conventional dental porcelain composition may be used to form the veneer.

The very thin electroplated deposit of gold which is relatively uniformly applied over the surface of the understructure locks the beaded gold particles in place. The beaded gold particles in turn provide a retentive surface for the porcelain which is highly resistant to fracture. The electroplated gold surface is too thin by itself to propagate a strain fracture and the varying size gold particles tend to force redirection of the strain forces.

What is claimed is:

1. A method of manufacturing a fixed prosthodontic metal ceramic dental restoration comprising casting a metal framework from a metal composition comprising an alloy of nickel and chromium having at least 4% nickel, electroplating a thin film deposit of gold between about 0.4 to 1 mil in thickness over a predetermined surface area of said framework with said gold deposit being in intimate contact with the nickel chromium alloy; distributing finely divided particles containing a major proportion of gold which vary in size between 1 to no more than about 20 microns over said electroplated gold surface and firing successive layers of porcelain over said predetermined surface area in a firing temperature range of between about 1600° F. to 1900° F. whereby the firing of said porcelain layers simultaneously causes said finely divided particles to form beads of substantially globular shape.

2. A method as defined in claim 1 wherein said nickel is at least 20%.

3. A method as defined in claim 2 wherein said finely divided particles are suspended in a carrier adapted to volatilize within the firing range of said porcelain.

4. A method as defined in claim 3 wherein said finely divided particles containing gold comprises an alloy substantially of gold with a minor concentration of elements selected from the class consisting of B, Al, Mg, Cu and Si.

5. A method as defined in claim 4 wherein said framework comprises the following composition by weight: 20–25% Cr; 1.7% Be; about 70–75% Ni with trace elements of Fe, Si, C and B.

* * * * *